(12) United States Patent
Szewczyk et al.

(10) Patent No.: US 10,576,033 B2
(45) Date of Patent: Mar. 3, 2020

(54) DENTIFRICE COMPRISING ZINC-AMINO ACID COMPLEX

(71) Applicant: Colgate-Palmolive Company, New York, NY (US)

(72) Inventors: Gregory Szewczyk, Flemington, NJ (US); Lauren Evans, Piscataway, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/756,362

(22) PCT Filed: Dec. 13, 2017

(86) PCT No.: PCT/US2017/066060
§ 371 (c)(1),
(2) Date: Feb. 28, 2018

(87) PCT Pub. No.: WO2019/117887
PCT Pub. Date: Jun. 20, 2019

(65) Prior Publication Data
US 2019/0175478 A1 Jun. 13, 2019

(51) Int. Cl.
| | |
|---|---|
| *A61K 8/58* | (2006.01) |
| *A61K 8/21* | (2006.01) |
| *A61K 8/24* | (2006.01) |
| *A61K 8/46* | (2006.01) |
| *A61K 8/73* | (2006.01) |
| *A61K 8/81* | (2006.01) |
| *A61K 8/25* | (2006.01) |
| *A61K 8/86* | (2006.01) |
| *A61K 8/44* | (2006.01) |
| *A61Q 11/00* | (2006.01) |
| *A61K 8/19* | (2006.01) |
| *A61K 8/27* | (2006.01) |

(52) U.S. Cl.
CPC .............. *A61K 8/58* (2013.01); *A61K 8/19* (2013.01); *A61K 8/21* (2013.01); *A61K 8/24* (2013.01); *A61K 8/25* (2013.01); *A61K 8/27* (2013.01); *A61K 8/44* (2013.01); *A61K 8/442* (2013.01); *A61K 8/463* (2013.01); *A61K 8/731* (2013.01); *A61K 8/8176* (2013.01); *A61K 8/86* (2013.01); *A61Q 11/00* (2013.01); *A61K 2800/48* (2013.01); *A61K 2800/58* (2013.01)

(58) Field of Classification Search
None
See application file for complete search history.

(56) References Cited

U.S. PATENT DOCUMENTS

| | | | | |
|---|---|---|---|---|
| 9,572,756 B2 * | 2/2017 | Liu | ............. | A61K 8/27 |
| 9,675,823 B2 * | 6/2017 | Liu | ............. | A61K 8/46 |
| 9,757,316 B2 * | 9/2017 | Pan | ............. | A61K 8/27 |
| 9,763,865 B2 * | 9/2017 | Pan | ............. | A61K 8/27 |
| 9,775,792 B2 * | 10/2017 | Liu | ............. | A61K 8/27 |
| 9,913,784 B2 * | 3/2018 | Szewczyk | ............. | A61K 8/27 |
| 9,980,890 B2 * | 5/2018 | Pan | ............. | A61K 8/27 |
| 10,105,303 B2 * | 10/2018 | Pan | ............. | A61K 8/27 |
| 10,130,571 B2 * | 11/2018 | Szewczyk | ............. | A61K 8/24 |

FOREIGN PATENT DOCUMENTS

| | | | | |
|---|---|---|---|---|
| CA | 2892419 A1 * | 6/2014 | ............. | A61K 8/27 |
| WO | WO-9112517 A1 * | 3/1999 | ............. | A61K 8/24 |
| WO | 2014/098813 | 6/2014 | | |
| WO | 2014/098818 | 6/2014 | | |
| WO | 2015/195124 | 12/2015 | | |

* cited by examiner

*Primary Examiner* — Michael P Cohen

(57) ABSTRACT

Disclosed herein are dentifrices comprising a zinc-amino acid complex together with a thickening system comprising a non-ionic thickening agent, which have a pH greater than 8.0. Methods of using the dentifrices are also provided.

12 Claims, No Drawings

DENTIFRICE COMPRISING ZINC-AMINO ACID COMPLEX

BACKGROUND

Dental erosion involves demineralization and damage to the tooth structure due to acid attack from nonbacterial sources. Erosion is found initially in the enamel and, if unchecked, may proceed to the underlying dentin. Dental erosion may be caused or exacerbated by acidic foods and drinks, exposure to chlorinated swimming pool water, and regurgitation of gastric acids. The tooth enamel is a negatively charged surface, which naturally tends to attract positively charged ions such as hydrogen and calcium ions, while resisting negatively charged ions such as fluoride ions, Depending upon relative pH of surrounding saliva, the tooth enamel will lose or gain positively charged ions such as calcium ions. Generally saliva has a pH between 7.2 to 7.4. When the pH is lowered and concentration of hydrogen ions becomes relatively high, the hydrogen ions will replace the calcium ions in the enamel, forming hydrogen phosphate (phosphoric acid), which damages the enamel and creates a porous, sponge-like roughened surface. If saliva remains acidic over an extended period, then remineralization may not occur, and the tooth will continue to lose minerals, causing the tooth to weaken and ultimately to lose structure.

Dentinal hypersensitivity is acute, localized tooth pain in response to physical stimulation of the dentine surface as by thermal (hot or cold) osmotic, tactile combination of thermal, osmotic and tactile stimulation of the exposed dentin. Exposure of the dentine, which is generally due to recession of the gums, or loss of enamel, frequently leads to hypersensitivity. Dentinal tubules open to the surface have a high correlation with dentine hypersensitivity. Dentinal tubules lead from the pulp to the cementum. When the surface cementum of the tooth root is eroded, the dentinal tubules become exposed to the external environment. The exposed dentinal tubules provide a pathway for transmission of fluid flow to the pulpal nerves, the transmission induced by changes in temperature, pressure and ionic gradients.

Heavy metal ions, such as zinc, are resistant to acid attack. Zinc ranks above hydrogen in the electrochemical series, so that metallic zinc in an acidic solution will react to liberate hydrogen gas as the zinc passes into solution to form di-cations, $Zn^{2+}$. Deposition of zinc on the teeth therefore helps to protect the teeth against acid erosion.

Zinc has also been shown to have antibacterial properties in plaque and caries studies.

Soluble zinc salts, such as zinc citrate, have been used in dentifrice compositions but have several disadvantages. Zinc ions in solution impart an unpleasant, astringent mouthfeel, so formulations that provide effective levels of zinc, and also have acceptable organoleptic properties, have been difficult to achieve. Finally, the zinc ions will react with anionic surfactants such as sodium lauryl sulfate, thus interfering with foaming and cleaning. Zinc oxide and insoluble zinc salts, on the other hand, may do a poor job of delivering zinc to the teeth because of their insolubility.

The zinc-amino acid complex forms a soluble cationic moiety, which in turn may form a salt with a halide or other anion. A zinc-lysine complex ("ZLC") having the chemical structure $[Zn(C_6H_{14}N_2O_2)_2Cl]^+Cl^-$, has been described. See, e.g. PCT/US2012/070489 and PCT/US2012/070498, and each incorporated by reference in its entirety. ZLC has the unusual property that under conditions of increasing dilution, rather than going into or remaining in solution as the solution becomes more dilute, as would typically be the case for an ionic complex, the ZLC dissociates to provide a relatively insoluble zinc oxide precipitate. When placed in formulation, this complex provides an effective concentration of zinc ions to the enamel, thereby protecting against erosion, reducing bacterial colonization and biofilm development, and providing enhanced shine to the teeth. Moreover, upon use, the formulation provides a precipitate that can plug the dentinal tubules, thereby reducing the sensitivity of the teeth. While providing efficient delivery of zinc in comparison to formulations with insoluble zinc salts, the formulations comprising the zinc-lysine complex do not exhibit the poor taste and mouthfeel, poor fluoride delivery, and poor foaming and cleaning associated with conventional zinc-based oral care products using soluble zinc salts.

While the prior art discloses the use of various oral compositions for the treatment of dentinal hypersensitivity, dental caries, and enamel erosion and demineralization, there is still a need for additional compositions and methods that provide improved performance in such treatments.

BRIEF SUMMARY

It has been found that when non-ionic polymers, e.g., hydroxyethyl cellulose, are added to dentifrice formulations comprising zinc-amino acid complexes, the non-ionic polymers surprisingly improve the rheological properties of the dentifrice formulations. When anionic polymers, e.g., xanthan gum or carboxymethyl cellulose (CMC) are used as thickening agents in the formulation comprising zinc-amino acid complexes, the formulation becomes too viscous. This problem is solved by substituting non-ionic polymers, e.g., hydroxyethyl cellulose, for anionic polymers.

It has also been found that when the dentifrice formulations comprising zinc-amino acid complexes are slightly basic with a pH greater than pH 8.0, e.g., 8.0-8.5, or about 8.2, the complexes rapidly dissociate to provide a relatively insoluble zinc oxide precipitate upon dilution with water and saliva during use, compared to dentifrice compositions having a neutral pH, while the complexes are stable in the dentifrice formulations prior to use.

The invention thus provides a dentifrice composition, for example an oral gel or toothpaste, that comprises
 (i) a zinc-amino acid complex, e.g., a zinc-lysine-chloride complex, e.g., ZLC; and
 (ii) a thickening system comprising a non-ionic thickening agent, e.g., hydroxyethyl cellulose and polyvinylpyrrolidone.

In some embodiments, the composition has a pH greater than 8.0, e.g., 8.0-9.0, 8.0-8.5, 8.1-8.3, or about 8.2.

The invention further provides methods of using the compositions of the invention to reduce and inhibit acid erosion of the enamel, clean the teeth, reduce bacterially-generated biofilm and plaque, reduce gingivitis, inhibit tooth decay and formation of cavities, and reduce dentinal hypersensitivity, comprising applying a composition of the invention to the teeth.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

DETAILED DESCRIPTION

The following description of the preferred embodiment(s) is merely exemplary in nature and is in no way intended to limit the disclosure, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The invention provides, in a first embodiment, a dentifrice (Composition 1.0), for example an oral gel or toothpaste, that comprises
  (i) a zinc-amino acid complex, e.g., a zinc-lysine-chloride complex, e.g., ZLC; and
  (ii) a thickening system comprising a non-ionic thickening agent, For example, the invention includes:

1.1. Composition 1.0 wherein the amino acid is selected from lysine, glycine and arginine, in free or orally acceptable acid addition salt form, e.g., hydrochloride form.
1.2. Composition 1.0 or 1.1, wherein the amino acid is a basic amino acid, e.g., arginine or lysine, in free or orally acceptable salt form.
1.3. Any of the foregoing compositions further comprising a halide in ionic association with the zinc and amino acid.
1.4. Any of the foregoing compositions wherein the molar ratio of Zn:amino acid is from 3:1 to 1:5, e.g., about 1:2 and the molar ratio of Zn:halide where present is from 3:1 to 1:3, e.g., about 1:2.
1.5. Any of the foregoing compositions wherein the zinc-amino acid complex is formed, in whole or in part, in situ after the composition is formulated.
1.6. Any of the foregoing compositions wherein the zinc-amino acid complex is added to the composition as a pre-formed salt, e.g., crystalline $[Zn(C_6H_{14}N_2O_2)_2Cl]^+Cl^-$.
1.7. Any of the foregoing compositions, wherein the amino acid is lysine.
1.8. Any of the foregoing compositions, wherein zinc is present in an amount of 0.05 to 10% by weight of the composition, optionally at least 0.1, at least 0.2, at least 0.3, at least 0.4, at least 0.5, at least 1, at least 2, at least 3, or at least 4 up to 10% by weight of the composition, e.g. about 1-3%, e.g., about 2-2.7% by weight of the composition.
1.9. Any of the foregoing compositions, wherein amino acid is present in an amount of 0.05 to 30% by weight of the composition, optionally at least 0.1%, at least 0.2%, at least 0.3%, at least 0.4%, at least 0.5%, at least 1%, at least 2%, at least 3%, at least 4%, at least 5%, at least 10%, at least 15%, at least 20% up to 30%, e.g., about 1-10% by weight of the composition.
1.10. Any of the foregoing compositions, wherein a molar ratio of zinc to amino acid is 2:1 to 1:4, optionally 1:1 to 1:4, 1:2 to 1:4, 1:3 to 1:4, 2:1 to 1:3, 2:1 to 1:2, or 2:1 to 1:1, e.g., about 1:2 or 1:3
1.11. Any of the foregoing compositions comprising a halide in ionic association with the zinc and amino acid, wherein the halide is selected from the group consisting of fluorine, chlorine, and mixtures thereof.
1.12. Any of the foregoing compositions wherein the zinc amino acid complex is a zinc lysine chloride complex (e.g., $(ZnLys_2Cl)^+Cl^-$ or $(ZnLys_3)^{2+}Cl_2$) or a zinc arginine chloride complex.
1.13. Any of the foregoing compositions, wherein the zinc amino acid complex is a zinc lysine chloride complex, e.g., ZLC, e.g., a zinc lysine chloride complex having the chemical structure $[Zn(C_6H_{14}N_2O_2)_2Cl]^+Cl^-$, either in solution of the cationic complex (e.g., $[Zn(C_6H_{14}N_2O_2)_2Cl]^+$) and the chloride anion, or in solid salt form, e.g., crystal form, optionally in mono- or dihydrate form.
1.14. Any of the foregoing compositions, wherein the zinc amino acid complex is a zinc lysine chloride complex having the chemical structure $[Zn(C_6H_{14}N_2O_2)_2Cl]^+Cl^-$, wherein the Zn cation is coordinated by two lysine ligands with two N atoms from $NH_2$, groups and O atoms from carboxylic groups in an equatorial plane, to form a cation with distorted square-pyramidal geometry with the apical position occupied by a Cl atom, to which cation a Cl anion is combined to form an ionic salt.
1.15. Any of the foregoing compositions in the form of a clear gel which provides a zinc oxide precipitate when diluted.
1.16. Any of the foregoing compositions, wherein the zinc-amino acid complex is present in an effective amount, e.g., in an amount of 0.5-4% of zinc, e.g., about 1-3% of zinc by weight of the composition.
1.17. Any of the foregoing compositions, wherein the zinc-amino acid complex is $[Zn(C_6H_{14}N_2O_2)_2Cl]^+Cl^-$ and is present in an amount of 3%-9%, 4%-8%, 5%-7%, or 5.5-6.5%, e.g., about 6% by weight of the composition.
1.18. Any of the foregoing compositions, wherein the composition comprises an abrasive, e.g., an effective amount of a silica abrasive, e.g., 10-30%, e.g., about 20%, by weight of the composition.
1.19. Any of the foregoing compositions wherein the zinc-amino acid complex is present in an effective amount, e.g., in an amount of 0.1-3% of zinc, e.g., about 0.2-1% of zinc by weight of the composition.
1.20. Any of the foregoing compositions wherein the zinc-amino acid complex is ZLC.
1.21. Any of the foregoing compositions wherein the zinc-amino acid complex is present in an amount of 2-10%, 2-8%, 4-8%, 5-8%, 5-7%, or 5.5-6.5%, e.g., 6%, by weight of the composition.
1.22. Any of the foregoing compositions, wherein the non-ionic thickening agent is present in an amount of 1-15%, 5-12%, 7-11%, 8-10%, 1-10%, 2-8%, or 5-7%, by weight of the composition.
1.23. Any of the foregoing compositions, wherein the non-ionic thickening agent is selected from the group consisting of hydroxyethyl cellulose, hydroxybutyl methyl cellulose, hydroxypropyl methylcellulose, polyethylene glycols, e.g., polyethylene glycol 600, polyvinylpyrrolidone, starch, and mixtures thereof.
1.24. Any of the foregoing compositions, wherein the non-ionic thickening agent comprises hydroxyethyl cellulose in an amount of 0.05-5%, 0.05-0.5%, 0.1-0.5%, or 0.1-0.3%, e.g., about 0.2%, by weight of the composition.
1.25. Any of the foregoing compositions, wherein the non-ionic thickening agent comprises polyvinylpyrrolidone in an amount of 0.2-5%, 0.5-2%, or 0.5-1.5%, e.g., 1%, by weight of the composition.

1.26. Any of the foregoing compositions, wherein the non-ionic thickening agent comprises polyethylene glycol, e.g., polyethylene glycol 600, in an amount of 1-6%, or 2-4%, e.g., 3%, by weight of the composition.
1.27. Any of the foregoing compositions, wherein the non-ionic thickening agent comprises hydroxyethyl cellulose and polyvinylpyrrolidone.
1.28. Any of the foregoing compositions, wherein the non-ionic thickening agent comprises 0.05-0.5%, 0.1-0.5%, or 0.1-0.3%, e g., about 0.2 wt. %, hydroxyethyl cellulose and 0.5-2% or 0.5-1.5%, e.g., about 1%, polyvinylpyrrolidone, by weight of the composition.
1.29. Any of the foregoing compositions, wherein the non-ionic thickening agent comprises hydroxyethyl cellulose, polyvinylpyrrolidone and polyethylene glycol, e.g., polyethylene glycol 600.
1.30. Any of the foregoing compositions, wherein the non-ionic thickening agent comprises 0.05-0.5%, 0.1-0.5%, or 0.1-0.3%, e.g., about 0.2 wt. %, hydroxyethyl cellulose, 0.5-2% or 0.5-1.5%, e.g., about 1%, polyvinylpyrrolidone and 1-6%, or 2-4%, e.g., 3%, polyethylene glycol, e.g., polyethylene glycol 600, by weight of the composition.
1.31. Any of the foregoing compositions, wherein the thickening system further comprises a silica thickener.
1.32. Any of the foregoing compositions, wherein the silica thickener is present in an amount of 1-10%, 2-8%, 5-8%, or 5-7%, e.g., about 6%, by weight of the composition.
1.33. Any of the foregoing compositions, wherein the composition comprises 0.05-0.5%, 0.1-0.5%, or 0.1-0.3%, e.g., about 0.2 wt. %, hydroxyethyl cellulose, 0.5-2% or 0.5-1.5%, e.g., about 1%, polyvinylpyrrolidone, 1-6%, or 2-4%, e.g., 3%, polyethylene glycol, e.g., polyethylene glycol 600, and 2-8% or 5-7%, e.g., about 6%, silica thickener, by weight of the composition.
1.34. Any of the foregoing compositions, wherein the composition does not contain any anionic polysaccharide thickening agent, e.g., xanthan gum and carboxymethyl cellulose.
1.35. Any of the foregoing compositions, wherein the composition does not contain any anionic polymer thickening agent.
1.36. Any of the foregoing compositions, wherein the composition is slightly basic, e.g., the composition has a pH greater than 8.0.
1.37. Any of the foregoing compositions, wherein the pH of the composition is 8.0-9.0, 8.0-8.5, 8.0-8.4, 8.0-8.3, 8.1-8.5, 8.1-8.4, 8.1-8.3, 8.2-8.5, 8.2-8.4, 8.2-8.3, or about 8.2.
1.38. Any of the foregoing compositions further comprising one or more soluble phosphate salts, e.g. selected from tetrasodium pyrophosphate (TSPP), sodium tripolyphosphate (STPP) and combinations thereof
1.39. Any of the foregoing compositions wherein by "soluble phosphate salts" is meant an orally acceptable phosphate salt having a solubility in water of at least 1 g/100 ml at 25° C.
1.40. Any of the foregoing compositions wherein the one or more soluble phosphate salts are sodium and/or potassium salts of pyrophosphates and/or polyphosphates, e.g., tripolyphosphates.
1.41. Any of the foregoing compositions wherein the one or more soluble phosphate salts comprise tetrasodium pyrophosphate (TSPP), sodium tripolyphosphate (STPP) or a combination of TSPP and STPP.
1.42. Any of the foregoing compositions wherein the one or more soluble phosphate salts are present in an amount of 1-20%, e.g., 1-10%, 5-10%, 2-8%, or 1-3%, e.g., about 2%, by weight of the composition.
1.43. Any of the foregoing compositions further comprising an effective amount of a fluoride ion source, e.g., providing 500 to 3000 ppm fluoride.
1.44. Any of the foregoing compositions wherein the fluoride is a salt selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.
1.45. Any of the foregoing compositions wherein the composition comprises a humectant, e.g., selected from glycerin, sorbitol, propylene glycol, polyethylene glycol, xylitol, and mixtures thereof, e.g. comprising at least 30%, e.g., 30-50% glycerin, by weight of the composition.
1.46. Any of the preceding compositions wherein composition comprises one or more surfactants, e.g., selected from anionic, cationic, zwitterionic, and non-ionic surfactants, and mixtures thereof.
1.47. Any of the preceding compositions wherein the composition comprises an anionic surfactant, e.g., a surfactant selected from sodium lauryl sulfate, sodium ether lauryl sulfate, and mixtures thereof, e.g. in an amount of from about 0.3% to about 4.5% by weight, e.g. 1-2% sodium lauryl sulfate (SLS) by weight of the composition.
1.48. Any of the preceding compositions wherein the composition comprises a zwitterionic surfactant, for example a betaine surfactant, for example cocamidopropylbetaine, e.g. in an amount of 0.1%-4.5% by weight, e.g. 0.5-2% cocamidopropylbetaine by weight of the composition
1.49. Any of the preceding compositions wherein the composition comprises gum strips or fragments.
1.50. Any of the preceding compositions wherein the composition comprises flavoring, fragrance and/or coloring.
1.51. Any of the foregoing compositions wherein the composition comprises an effective amount of one or more antibacterial agents in addition to the zinc-amino acid complex, for example comprising an antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, seabuckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing; e.g., comprising triclosan or cetylpyridinium chloride.

1.52. Any of the foregoing compositions wherein the composition comprises an antibacterially effective amount of triclosan, e.g. 0.1-0.5%, e.g. about 0.3% by weight of the composition.

1.53. Any of the preceding compositions wherein the composition comprises a whitening agent, e.g., a selected from the group consisting of peroxides, metal chlorites, perborates, percarbonates, peroxyacids, hypochlorites, and combinations thereof.

1.54. Any of the preceding compositions wherein the composition comprises hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate);

1.55. Any of the preceding compositions wherein the composition comprises an agent that interferes with or prevents bacterial attachment, e.g., solbrol or chitosan.

1.56. Any of the preceding compositions wherein the composition comprises a soluble calcium salt, e.g., selected from calcium sulfate, calcium chloride, calcium nitrate, calcium acetate, calcium lactate, and combinations thereof.

1.57. Any of the preceding compositions wherein the composition comprises a physiologically or orally acceptable potassium salt, e.g., potassium nitrate or potassium chloride, in an amount effective to reduce dentinal sensitivity.

1.58. Any of the preceding compositions wherein the composition comprises a breath freshener, fragrance or flavoring.

1.59. Any of the foregoing compositions, wherein the composition comprises water in the amount of 1-20%, e.g., 10-20%, 10-18%, 12-18%, 10-15%, 15-20%, 12-16%, 4-16%, 14%-18%, e.g., about 15%, by weight of the composition.

1.60. Any of the foregoing compositions wherein
the zinc-amino acid complex is ZLC in an amount of 2-8% by weight of the composition; and
the composition comprise 0.1-0.5%, e.g., about 0.2 wt. %, hydroxyethyl cellulose, 0.5-2%, e.g., about 1%, polyvinylpyrrolidone, 2-4%, e.g., about 3%, polyethylene glycol 600, and 1-10%, e.g., about 6%, silica thickener by weight of the composition; and
the composition further comprises
an effective amount of a fluoride ion source,
silica abrasives,
humectant,
one or more soluble phosphate salts, e.g., sodium tripolyphosphate (STPP), anionic surfactant, e.g., sodium lauryl sulfate,
zwitterionic surfactant, e.g., cocamidopropyl betaine,
flavoring, sweetener and 10-18%, e.g., about 15%, water by weight of the composition, and
the pH of the composition is 8.1-8.3, e.g., about 8.2.

1.61. Any of the forgoing compositions for use to reduce and inhibit acid erosion of the enamel, clean the teeth, reduce bacterially-generated biofilm and plaque, reduce gingivitis, inhibit tooth decay and formation of cavities, and reduce dentinal hypersensitivity.

The invention further provides methods to reduce and inhibit acid erosion of the enamel, clean the teeth, reduce bacterially-generated biofilm and plaque, reduce gingivitis, inhibit tooth decay and formation of cavities, and reduce dentinal hypersensitivity, comprising applying an effective amount of a composition of the invention, e.g., any of Composition 1, et seq. to the teeth, and optionally then rinsing with water or aqueous solution sufficient to trigger precipitation of zinc oxide from the composition.

For example, in various embodiments, the invention provides methods to (i) reduce hypersensitivity of the teeth, (ii) to reduce plaque accumulation, (iii) reduce or inhibit demineralization and promote remineralization of the teeth, (iv) inhibit microbial biofilm formation in the oral cavity, (v) reduce or inhibit gingivitis, (vi) promote healing of sores or cuts in the mouth, (vii) reduce levels of acid producing bacteria, (viii) to increase relative levels of non-cariogenic and/or non-plaque forming bacteria, (ix) reduce or inhibit formation of dental caries, (x), reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity, (xiii) reduce erosion, (xiv) whiten teeth; (xv) reduce tartar build-up, and/or (xvi) promote systemic health, including cardiovascular health, e.g., by reducing potential for systemic infection via the oral tissues, comprising applying any of Compositions 1, et seq. as described above to the oral cavity of a person in need thereof, e.g., one or more times per day. The invention further provides Compositions 1, et seq. for use in any of these methods.

Irrespective of the precise structure of the zinc-amino acid complexes, the interaction of the zinc and the amino acid converts insoluble zinc oxide or zinc salts to a highly soluble complex at approximately neutral pH. With increasing dilution in water, however, the complexes dissociate and the zinc ion converts to insoluble zinc oxide. This facilitates deposition of the zinc precipitate on the teeth upon administration, in the presence of saliva and with rinsing. This precipitation occludes the dentinal tubules, thereby reducing hypersensitivity, and also provides zinc to the enamel, which reduces acid erosion, biofilm and plaque formation.

In the present invention, the zinc-amino acid complexes, e.g., a zinc-lysine-chloride complex, e.g., ZLC, are provided in a toothpaste. Upon brushing, the complexes are diluted by saliva and water, leading to precipitation and the formation of deposits and occluding particles. The rate of precipitation from the formulation can be modulated by adjusting concentration of the complex in the dentifrice formulation, and changing the amount of water. A more diluted formula leads to faster precipitation and is thus preferred when a fast treatment is desired. However, the more diluted formula can also lead to the premature formation of zinc oxide in the formulation prior to use.

It has been found that when the dentifrice formulations comprising zinc-amino acid complexes are slightly basic with a pH greater than 8.0, e.g., 8.0-9.0, 8.0-8.5, or 8.1-8.3, e.g., about 8.2, the complexes rapidly dissociates to provide a relatively insoluble zinc oxide precipitate upon dilution during use, compared to dentifrice compositions having a neutral pH, while the zinc-amino acid complexes remains stable in the slightly basic dentifrice formulations prior to use. Without intending to be bound by theory, it is believed that the zinc-amino acid complex is more prone to dissociate in a higher pH when the zinc-amino acid complexes are diluted with water and saliva. However, it is believed that the complexes remain stable in the slightly basic dentifrice formulations at least partly because the complexes are more stable in the less diluted condition and other ingredients contained in the dentifrice composition preserve the complex. For example, soluble phosphate salts are known to preserve the complex. See PCT/US2014/043051, being incorporated by reference in its entirety. Thus, the invention provides dentifrice compositions comprising a zinc-amino acid complex, e.g., a zinc-lysine-chloride complex, e.g., ZLC, which are stable when formulated, but which rapidly provide a zinc oxide precipitate when diluted with water and saliva. In addition, it has been found that below pH 8.0 the formula species are too promiscuous internally and react with other ingredients in the dentifrice formulation comprising zinc-amino acid complexes. In certain embodiments, the composition has a pH greater than 8.0, e.g., 8.0-9.0, 8.0 -8.5, 8.0-8.4, 8.0-8.3, 8.1-8.5, 8.1-8.4, 8.1-8.3, 8.2-8.5, 8.2-8.4, 8.2-8.3, or about 8.2. The pH is that measured when the dentifrice composition is slurried with water in a 1:3 weight ratio of the composition to water.

The composition of the invention comprises a thickening system comprising a non-ionic thickening agent, e.g., hydroxyethyl cellulose. Polymers are added into the dentifrice composition to adjust the viscosity of the formulation or enhance the solubility of other ingredients. However, dentifrice compositions containing zinc-amino acid complexes in combination with thickening agents commonly used in the dentifrice composition such as carboxymethyl cellulose and xanthan gum can suffer from the technical problem of poor rheological properties. In particular, the dentifrice composition comprising a high amount of zinc-amino acid complexes can exhibit an unacceptably high viscosity, which can make the composition difficult to dispense from the dispenser and difficult to disperse in the mouth during tooth brushing, resulting in a poor feeling in the mouth for the consumer. Such dentifrice compositions can also tend to exhibit progressive thickening over time. Without intending to be bound by theory, it is possible that the unacceptably high viscosity may be due to disruption of the zinc-amino acid complexes by the carboxylate groups of the thickening agents included in the dentifrice composition, which can chelate the zinc ions and form ionic bridges, leading to an unacceptably high viscosity in the dentifrice composition.

It has been found, however, that the use of a thickening agent that does not have anionic groups either as the sole thickening agent or as one of a plurality of thickening agents provides no site for ionic interaction with zinc ions or with the cationic portion of the zinc-amino acid complexes. This in turn allows for the incorporation of higher levels of zinc-amino acid complexes than would be possible using other thickening systems, for example based on carboxymethyl cellulose (CMC) or xanthan gum formulas, without unacceptable increase in viscosity.

Thus, the oral care compositions of the invention include thickening agents that do not have anionic groups, e.g., carboxylate groups. Thickening agents suitable for this invention may include any non-ionic thickening agents that can adjust the viscosity of the composition. For example, the non-ionic thickening agents suitable for this invention include nonionic polysaccharides (e.g., hydroxyethyl cellulose, hydroxybutyl methyl cellulose, hydroxypropyl methylcellulose), polyethylene glycols, e.g., polyethylene glycol 600, polyvinylpyrrolidone, preferably PLASDONE K-90® (a registered trademark of International Specialty Products), starch, and mixtures thereof. In certain embodiments, the compositions comprise nonionic polysaccharides, e.g., hydroxyethyl cellulose, hydroxybutyl methyl cellulose, hydroxypropyl methylcellulose. Preferably, the compositions comprise hydroxyethyl cellulose. In certain embodiments, the compositions comprise a mixture of nonionic polysaccharides and other non-ionic polymers that are not polysaccharides, e.g., polyethylene glycol and polyvinylpyrrolidone. In certain embodiments, the compositions comprise hydroxyethyl cellulose, polyethylene glycol and polyvinylpyrrolidone. Nonionic polysaccharides, e.g., hydroxyethyl cellulose, may be present in an amount of 0.05-5%, 0.05-0.5%, 0.1-0.5%, or 0.1-0.3%, e.g., about 0.2%, by weight of the composition. Polyethylene glycol may be present in an amount of 1-6%, or 2-4%, e.g., 3%, by weight of the composition. Polyvinylpyrrolidone may be present in an amount of 0.2-5%, 0.5-2%, or 0.5-1.5%, e.g., 1%, by weight of the composition.

The oral care compositions of the invention may further comprise silica thickeners, which form polymeric structures or gels in aqueous media. These silica thickeners are physically and functionally distinct from the particulate silica abrasives also present in the compositions, as the silica thickeners are very finely divided and provide little or no abrasive action. Silica thickeners may be present in an amount of 1-10%, 2-8%, 5-8%, or 5-7%, e.g., about 6%, by weight of the composition.

In certain embodiments, the compositions comprise hydroxyethyl cellulose and silica thickeners. In certain embodiments, the compositions comprise hydroxyethyl cellulose, polyethylene glycol, polyvinylpyrrolidone and silica thickener.

The total amount of nonionic thickening agents present in the composition may be 1-15%, 1-10%, 5-12%, 7-11%, 8-10%, 2-8%, or 5-7%, by weight of the composition.

In certain embodiments, the compositions do not contain any polysaccharide thickening agent containing anionic groups (e.g., carboxylate groups), for example carboxymethyl cellulose (CMC) and xanthan gum. In certain embodiments, the compositions do not contain any polymer thickening agent containing anionic groups (e.g., carboxylate groups).

It is believed that the formation of the zinc amino acid halide proceeds via formation of the zinc halide then coordination of amino acid residues around a central zinc. Using reaction of ZnO with lysine hydrochloride in water as an example, the zinc can react with lysine and/or lysine HCl to form a clear solution of Zn-lysine-chloride complex ($ZnLys_3Cl_2$), wherein $Zn^{++}$ is located in an octahedral center coordinated with two oxygen and two nitrogen atoms in the equatorial plane coming from two lysine's carboxylic acids and amine groups respectively. The zinc is also coordinated to the third lysine via its nitrogen and carboxylic oxygen, at the apical position of the metal geometry.

In another embodiment, a zinc cation is complexes with two amino acid residues and two chloride residues. For example, where the amino acid is lysine, the complex has the formula $[Zn(C_6H_{14}N_2O_2)_2Cl]^+Cl^-$. In this complex, Zn cation is coordinated by two lysine ligands with two N atoms from $NH_2$ groups and O atoms from carboxylic groups in an equatorial plane. It displays a distorted square-pyramidal geometry with the apical position occupied by a $Cl^-$ atom. This novel structure gives rise to a positive cation moiety, to which a $Cl^-$ anion is combined to form an ionic salt.

Other complexes of zinc and amino acid are possible, and the precise form is dependent in part on the molar ratios of the precursor compounds, e.g., if there is limited halide, halide-free complexes may form, e.g. $ZnOLys_2$, having a pyramid geometry, with the equatorial plane that is same as the above compound (Zn is bound to two oxygen and two nitrogen atoms from different lysines), wherein the top of the pyramid is occupied by an O atom.

Mixtures of complexes and/or additional complex structures, e.g., involving multiple zinc ions based on the zinc structure, are possible and contemplated within the scope of the invention. When the complexes are in solid form, they may form crystals, e.g. in hydrated form.

It will be understood that other amino acids can be used in place of lysine in the foregoing scheme. It will also be understood that, although the zinc, amino acid and optionally halide may be primarily in the form of precursor materials or in the form of an ionic complex, there may be some degree of equilibrium, so that the proportion of material which is actually in complex compared to the proportion in precursor form may vary depending on the precise conditions of formulation, concentration of materials, pH, presence or absence of water, presence or absence of other charged molecules, and so forth.

The benefits of the oral care compositions of the invention are numerous. By providing zinc ions and zinc containing compounds that can release zinc ions in oral cavities, the oral care compositions of the invention provide antimicrobial, antiplaque, antigingivitis, anti-malodor, anticaries, and anticalculus benefits. The occluding particles and the surface deposits are compounds containing zinc (particularly ZnO), as well as other zinc derivatives which can release zinc ions into oral cavities and provide the various benefits as recognized above. Additional benefits include but are not limited to anti-attachment, anti-periodontitis and anti-bone loss, as well as promotion of wound healing.

A second benefit is the antierosive properties of zinc ions, which form antierosive deposits on tooth surfaces through oxidation and hydrolysis. The surface deposits, as well as the occluding particles, can react with and neutralize acids, thus protecting the dental surface from the erosive effects of the acids. In this regard, the more surface depositions/occlusion the treatments lead to, the more efficacious the treatments are, and therefore zinc-arginine and zinc-lysine are preferred. It is also noted that when the surface deposits and occluding particles neutralize acids, beneficial zinc ions and amino acids (infra) can be released, providing oral care benefits other than anti-erosion.

A third benefit is anti-sensitivity benefit as a result of the occlusion. Occlusion of dentin tubules leads to sensitivity relief.

A fourth benefit is the benefit associated with amino acids. The occluding particles and surface deposits contain the corresponding amino acids, such as arginine and lysine. These amino acids provide multiple benefits. For example, basic amino acids lead to higher pH of the plaque and can provide anticaries benefits. In addition, it is also expected that arginine can enhance the activity of arginolytic bacteria, leading to a more healthy plaque. Arginine is also known to promote wound healing and collagen integrity.

The composition can include the zinc amino acid halide and/or precursors thereof. Precursors, which can react in situ with water to form the zinc amino acid halide, include (i) zinc and an amino acid hydrohalide, or (ii) zinc chloride and amino acid, or (iii) a zinc ion source, an amino acid, and a halogen acid, or (iv) combinations of (i), (ii), and/or (iii). In one embodiment, the zinc amino acid halide can be prepared at room temperature by mixing the precursors in a solution, such as water. The in situ formation provides ease of formulation. The precursors can be used instead of first having to form the zinc amino acid halide.

The zinc amino acid halide is a water soluble complex formed from the halide acid addition salt of zinc (e.g., zinc chloride) and an amino acid, or from the halide acid addition salt of an amino acid (e.g., lysine hydrochloride) and zinc ion source, and/or from combination of all three of a halogen acid, an amino acid, and a zinc ion source.

Examples of amino acids include, but are not limited to, the common natural amino acids, e.g.: lysine, arginine, histidine, glycine, serine, threonine, asparagine, glutamine, cysteine, selenocysteine, proline, alanine, valine, isoleucine, leucine, methionine, phenylalanine, tyrosine, tryptophan, aspartic acid, and glutamic acid. In some embodiments the amino acid is a neutral or acidic amino acid, e.g., glycine.

The precipitation of zinc from the complex upon dilution with water is most notable when the complex is formed from a basic amino acid. Thus, where precipitation upon dilution is desired, a basic amino acid may be preferred. In some embodiments, therefore, the amino acid is a basic amino acid. By "basic amino acid" is meant the naturally occurring basic amino acids, such as arginine, lysine, and histidine, as well as any basic amino acid having a carboxyl group and an amino group in the molecule, which is water-soluble and provides an aqueous solution with a pH of about 7 or greater. Accordingly, basic amino acids include, but are not limited to, arginine, lysine, citrulline, ornithine, creatine, histidine, diaminobutanoic acid, diaminopropionic acid, salts thereof or combinations thereof in certain embodiments, the amino acid is lysine. In other embodiments, the amino acid is arginine.

The halide may be chlorine, bromine, or iodine, most typically chlorine. The acid addition salt of an amino acid and a halogen acid (e.g., HCl, HBr, or HI) is sometimes referred to herein as an amino acid hydrohalide. Thus one example of an amino acid hydrohalide is lysine hydrochloride. Another is glycine hydrochloride.

The zinc ion source for combination with an amino acid halide or an amino acid optionally plus halogen acid in this case may be, e.g., zinc oxide or zinc chloride.

In certain embodiments, the amount of zinc amino acid halide in the composition is 0.05 to 10% by weight of the composition. In certain embodiments, precursors, e.g., zinc and amino acid hydrohalide, are present in amounts such that when combined into the zinc amino acid halide, the zinc amino acid halide would be present in an amount of 0.05 to 10% by weight of the composition. In either of these embodiments, the amount of the zinc amino acid halide can be varied for the desired purpose, such as a dentifrice or a mouthwash. In other embodiments, the amount of the zinc amino acid halide is at least 0.1, at least 0.2, at least 0.3, at least 0.4, at least 0.5, at least 1, at least 2, at least 3, or at least 4 up to 10% by weight of the composition. In other embodiments, the amount of the zinc amino acid halide is less than 9, less than 8, less than 7, less than 6, less than 5, less than 4, less than 3, less than 2, less than 1, less than 0.5 to 0.05% by weight of the composition. In other embodiments, the amounts are 0.05 to 5%, 0.05 to 4%, 0.05 to 3%, 0.05 to 2%, 0.1 to 5%, 0.1 to 4%, 0.1 to 3%, 0.1 to 2%, 0.5 to 5%, 0.5 to 4%, 0.5 to 3%, or 0.5 to 2% by weight of the composition.

In certain embodiments, zinc is present in an amount of 0.05 to 10% by weight of the composition. In other embodiments, the amount of zinc is at least 0.1, at least 0.2, at least 0.3, at least 0.4, at least 0.5, at least 1, at least 2, at least 3, or at least 4 up to 10% by weight of the composition. In other embodiments, the amount of the zinc is less than 9, less than 8, less than 7, less than 6, less than 5, less than 4, less than 3, less than 2, less than 1, less than 0.5 to 0.05% by weight of the composition. In other embodiments, the amounts are 0.05 to 5%, 0.05 to 4%, 0.05 to 3%, 0.05 to 2%, 0.1 to 5%, 0.1 to 4%, 0.1 to 3%, 0.1 to 2%, 0.5 to 5%, 0.5 to 4%, 0.5 to 3%, or 0.5 to 2% by weight of the composition.

In certain embodiments, amino acid hydrohalide is present in an amount of 0.05 to 30% by weight. In other embodiments, the amount is at least 0.1, at least 0.2, at least 0.3, at least 0.4, at least 0.5, at least 1, at least 2, at least 3, at least 4, at least 5, at least 10, at least 15, at least 20 up to 30% by weight. In other embodiments, the amount is less than 30, less than 25, less than 20, less than 15, less than 10, less than 5, less than 4, less than 3, less than 2, or less than 1 down to 0.05% by weight of the composition.

Where precursor materials are present, they are preferably present in molar ratios approximately as required to produce the desired zinc amino acid halide, although an excess of one material or another may be desirable in certain formulations, e.g., to balance pH against other formulation constituents, to provide additional antibacterial zinc, or to provide amino acid buffer. Preferably, however, the amount of halide is limited, as constraining the level of halide somewhat encourages interaction between the zinc and the amino acid.

In some embodiments, the total amount of zinc in the composition is 0.05 to 8% by weight of the composition. In other embodiments, the total amount of zinc is at least 0.1, at least 0.2, at least 0.3, at least 0.4, at least 0.5, or at least 1 up to 8% by weight of the composition. In other embodiments, the total amount of zinc in the composition is less than 5, less than 4, less than 3, less than 2, or less than 1 to 0.05% by weight of the composition.

In certain embodiments, a molar ratio of zinc to amino acid is at least 2:1. In other embodiments, the molar ratio is at least 1:1, at least 1:2, at least 1:3, at least 1:4, 2:1 to 1:4, 1:1 to 1:4, 1:2 to 1:4, 1:3 to 1:4, 2:1 to 1:3, 2:1 to 1:2, 2:1 to 1:1, or 1:3. Above 1:4, it is expected that the zinc will be totally dissolved.

The carrier represents all other materials in the composition other than the zinc amino acid halide complex or its precursors. The amount of carrier is then the amount to reach 100% by adding to the weight of the zinc amino acid halide, including any precursors.

Active Agents: The compositions of the invention may comprise various agents which are active to protect and enhance the strength and integrity of the enamel and tooth structure and/or to reduce bacteria and associated tooth decay and/or gum disease, including or in addition to the zinc-amino acid-halide complexes. Effective concentration of the active ingredients used herein will depend on the particular agent and the delivery system used. It is understood that a toothpaste for example will typically be diluted with water upon use, while a mouth rinse typically will not be. Thus, an effective concentration of active in a toothpaste will ordinarily be 5-15× higher than required for a mouth rinse. The concentration will also depend on the exact salt or polymer selected. For example, where the active agent is provided in salt form, the counter ion will affect the weight of the salt, so that if the counter ion is heavier, more salt by weight will be required to provide the same concentration of active ion in the final product. Arginine, where present, may be present at levels from, e.g., about 0.1 to about 20 wt % (expressed as weight of free base), e.g., about 1 to about 10 wt % for a consumer toothpaste or about 7 to about 20 wt % for a professional or prescription treatment product. Fluoride where present may be present at levels of, e.g., about 25 to about 25,000 ppm, for example about 750 to about 2,000 ppm for a consumer toothpaste, or about 2,000 to about 25,000 ppm for a professional or prescription treatment product. Levels of antibacterial agents will vary similarly, with levels used in toothpaste being e.g., about 5 to about 15 times greater than used in mouthrinse. For example, a triclosan toothpaste may contain about 0.3 wt % triclosan.

Fluoride Ion Source: The oral care compositions may further include one or more fluoride ion sources, e.g., soluble fluoride salts. A wide variety of fluoride ion-yielding materials can be employed as sources of soluble fluoride in the present compositions. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. In certain embodiments, the oral care composition of the invention may also contain a source of fluoride ions or fluorine-providing ingredient in amounts sufficient to supply about 25 ppm to about 25,000 ppm of fluoride ions, generally at least about 500 ppm, e.g., about 500 to about 2000 ppm, e.g., about 1000 to about 1600 ppm, e.g., about 1450 ppm. The appropriate level of fluoride will depend on the particular application. A toothpaste for general consumer use would typically have about 1000 to about 1500 ppm, with pediatric toothpaste having somewhat less. A dentifrice or coating for professional application could have as much as about 5,000 or even about 25,000 ppm fluoride. Fluoride ion sources may be added to the compositions of the invention at a level of about 0.01 wt. % to about 10 wt. % in one embodiment or about 0.03 wt. % to about 5 wt. %, and in another embodiment about 0.1 wt. % to about 1 wt. % by weight of the composition in another embodiment. Weights of fluoride salts to provide the appropriate level of fluoride ion will obviously vary based on the weight of the counter ion in the salt.

Amino acids: In some embodiments, the compositions of the invention comprise an amino acid. In particular embodiments, the amino acid may be a basic amino acid. By "basic amino acid" is meant the naturally occurring basic amino acids, such as arginine, lysine, and histidine, as well as any basic amino acid having a carboxyl group and an amino group in the molecule, which is water-soluble and provides an aqueous solution with a pH of about 7 or greater. Accordingly, basic amino acids include, but are not limited to, arginine, lysine, citrulline, ornithine, creatine, histidine, diaminobutanoic acid, diaminopropionic acid, salts thereof or combinations thereof. In a particular embodiment, the basic amino acids are selected from arginine, citrulline, and ornithine. In certain embodiments, the basic amino acid is arginine, for example, 1-arginine, or a salt thereof.

In various embodiments, the amino acid is present in an amount of about 0.5 wt. % to about 20 wt. % of the total composition weight, about 0.5 wt. % to about 10 wt. % of the total composition weight, for example about 1.5 wt. %, about 3.75 wt. %, about 5 wt. %, or about 7.5 wt. % of the total composition weight in the case of a dentifrice, or for example about 0.5-2 wt. %, e.g., about 1% in the case of a mouthwash.

Abrasives: The compositions of the invention, e.g. Composition 1 et seq. include silica abrasives, and may comprise additional abrasives, e.g., a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4.2H_2O$, also sometimes referred to herein as DiCal) or calcium pyrophosphate; calcium carbonate abrasive; or abrasives such as sodium metaphosphate, potassium metaphosphate, aluminum silicate, calcined alumina, bentonite or other siliceous materials, or combinations thereof.

Other silica abrasive polishing materials useful herein, as well as the other abrasives, generally have an average particle size ranging between about 0.1 and about 30 microns, about between 5 and about 15 microns. The silica abrasives can be from precipitated silica or silica gels, such as the silica xerogels. Particular silica xerogels are marketed under the trade name Syloid® by the W.R. Grace & Co., Davison Chemical Division. The precipitated silica materials include those marketed by the J.M. Huber Corp. under the trade name Zeodent®, including the silica carrying the designation Zeodent 115 and 119. In certain embodiments, abrasive materials useful in the practice of the oral care compositions in accordance with the invention include silica gels and precipitated amorphous silica having an oil absorption value of less than about 100 cc/100 g silica and in the range of about 45 cc/100 g to about 70 cc/100 g silica. Oil absorption values are measured using the ASTA Rub-Out Method D281. In certain embodiments, the silicas are colloidal particles having an average particle size of about 3 microns to about 12 microns, and about 5 to about 10 microns. Low oil absorption silica abrasives particularly useful in the practice of the invention are marketed under the trade designation Sylodent XWA® by Davison Chemical Division of W.R. Grace &. Co., Baltimore, Md. 21203. Sylodent 650 XWA®, a silica hydrogel composed of particles of colloidal silica having a water content of 29% by weight averaging about 7 to about 10 microns in diameter, and an oil absorption of less than about 70 cc/100 g of silica is an example of a low oil absorption silica abrasive useful in the practice of the present invention.

Foaming agents: The oral care compositions of the invention also may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2,000,000 and in another embodiment about 800,000 to about 1,000,000. Polyox®, is the trade name for the high molecular weight polyoxyethylene produced by Union Carbide. The polyoxyethylene may be present in an amount of about 1% to about 90%, in one embodiment about 5% to about 50% and in another embodiment about 10% to about 20% by weight of the oral care carrier component of the oral care compositions of the present invention. Where present, the amount of foaming agent in the oral care composition (i.e., a single dose) is about 0.01 to about 0.9% by weight, about 0.05 to about 0.5% by weight, and in another embodiment about 0.1 to about 0.2% by weight.

Surfactants: The compositions useful in the invention may contain anionic surfactants, for example:
 i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate,
 ii. higher alkyl sulfates, such as sodium lauryl sulfate,
 iii. higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or K, for example sodium laureth-2 sulfate ($CH_3(CH_2)_{10}CH_2(OCH_2CH_2)_2OSO_3Na$).
 iv. higher alkyl aryl sulfonates such as sodium dodecyl benzene sulfonate (sodium lauryl benzene sulfonate)
 v. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., $C_{6-30}$ alkyl. In particular embodiments, the anionic surfactant is selected from sodium lauryl sulfate and sodium ether lauryl sulfate. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. For example, concentrations used or a mouthwash are typically on the order of one tenth that used for a toothpaste. In one embodiment, the anionic surfactant is present in a toothpaste at from about 0.3% to about 4.5% by weight, e.g., about 1.5%. The compositions of the invention may optionally contain mixtures of surfactants, e.g., comprising anionic surfactants and other surfactants that may be anionic, cationic, zwitterionic or nonionic. Generally, surfactants are those which are reasonably stable throughout a wide pH range. In certain embodiments, the anionic surfactants useful herein include the water-soluble salts of alkyl sulfates having about 10 to about 18 carbon atoms in the alkyl radical and the water-soluble salts of sulfonated monoglycerides of fatty acids having about 10 to about 18 carbon atoms. Sodium lauryl sulfate, sodium lauroyl sarcosinate and sodium coconut monoglyceride sulfonates are examples of anionic surfactants of this type. In a particular embodiment, the composition of the invention, e.g., Composition 1, et seq., comprises sodium lauryl sulfate.

The surfactant or mixtures of compatible surfactants can be present in the compositions of the present invention in about 0,1% to about 5.0%, in another embodiment about 0.3% to about 3.0% and in another embodiment about 0.5% to about 2.0% by weight of the total composition.

Tartar control agents: In various embodiments of the present invention, the compositions comprise an anticalculus (tartar control) agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. The invention thus may comprise phosphate salts. In particular embodiments, these salts are alkali phosphate salts, i.e., salts of alkali metal hydroxides or alkaline earth hydroxides, for example, sodium, potassium or calcium salts. "Phosphate" as used herein encompasses orally acceptable mono- and polyphosphates, for example, $P_{1-6}$ phosphates, for example monomeric phosphates such as monobasic, dibasic or tribasic phosphate; dimeric phosphates such as pyrophosphates; and multimeric phosphates, e.g., sodium hexametaphosphate. In particular examples, the selected phosphate is selected from alkali dibasic phosphate and alkali pyrophosphate salts, e.g., selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any two or more of these. In a particular embodiment, for example the compositions comprise a mixture of tetrasodium pyrophosphate ($Na_4P_2O_7$), calcium pyrophosphate ($Ca_2P_2O_7$), and sodium phosphate dibasic ($Na_2HPO_4$), e.g., in amounts of ca. 3-4% of the sodium phosphate dibasic and ca. 0.2-1% of each of the pyrophosphates. In another embodiment, the compositions comprise a mixture of tetrasodium pyrophosphate (TSPP) and sodium tripolyphosphate (STPP) ($Na_5P_3O_{10}$), e.g., in proportions of TSPP at about 1-2% and STPP at about 7% to about 10%. Such phosphates are provided in an amount effective to reduce erosion of the enamel, to aid in cleaning the teeth, and/or to reduce tartar buildup on the teeth, for example in an amount of 2-20%, e.g., ca. 5-15%, by weight of the composition.

Flavoring Agents: The oral care compositions of the invention may also include a flavoring agent. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of about 0.1 to about 5% by weight e.g. about 0.5 to about 1.5% by weight.

Preservatives: The dentifrice compositions of the invention may include a preservative. Suitable preservatives include, for example, sodium benzoate, potassium sorbate, methylisothiazolinone, paraben preservatives, for example methyl p-hydroxybenzoate, propyl p-hydroxybenzoate, and mixtures thereof.

Humectants: The dentifrice compositions of the present invention may include one or more humectants. Humectants can reduce evaporation and also contribute towards preservation by lowering water activity, and can also impart desirable sweetness or flavor to compositions. Suitable humectants include edible polyhydric alcohols such as glycerin, sorbitol, xylitol, propylene glycol as well as other polyols and mixtures of these humectants. Other useful materials may also include orally acceptable alcohols, or polymers, e.g., such as polyvinylmethyl ether maleic acid copolymers, polysaccharides (e.g. cellulose derivatives, for example carboxymethyl cellulose, or polysaccharide gums, for example xanthan gum or carrageenan gum). In some embodiments, the humectant can be present in an amount of from 20% to 60%, for example from 30% to 50%, for example from 40% to 45%, by weight of the composition.

Water: The oral care compositions of the invention may comprise significant levels of water. Water employed in the preparation of commercial oral compositions should be deionized and free of organic impurities. The amount of water in the compositions includes the free water which is added plus that amount which is introduced with other materials. In certain embodiments, the composition comprises water in the amount of 1-20%, e.g., 10-20%, 10-18%, 12-18%, 10-15%, 15-20%, 12-16%, 4-16%, 14%-18%, e.g. about 15%, by weight of the composition.

EXAMPLES

Example 1

Preparation of ZLC

The general reaction for formation of ZLC for this example is as follows:

$ZnO+2(Lysine.HCl)\rightarrow[Zn(Lysine)_2Cl]Cl.H_2O(ZLC)$

A 2:1 molar ratio of ZnO:Lysine.HCl suspension is prepared with stirring at room temperature for about 12 hours. The mixture is centrifuged. 1 ml of supernatant is transferred into an NMR tube. The NMR tube is then placed in a closed test tube filled with ethanol for crystal growth. A number of colorless, cubic crystals are formed after a week. The crystal structure of ZLC crystal is determined by single crystal X-ray diffraction. The dimension of this complex molecule is 1.7 nm*7.8 nm*4.3 nm. In this complex, Zn cation is coordinated by two lysine ligands with two N atoms from $NH_2$ groups and O atoms from carboxylic groups in an equatorial plane. It displays a distorted square-pyramidal geometry with the apical position occupied by a Cl atom. This novel structure gives rise to a positive cation moiety, to which a Cl anion is combined to form an ionic salt.

Laboratory scale-up synthesis of pure ZLC powder: 2 mole of LysineHCl is dissolved in 1000 ml DI water with stirring at room temperature, 1 mole of solid ZnO is added slowly to the LysineHCl solution with stirring and the stirring is continued at RT overnight (about 12 hours). The suspension solution is centrifuged at high speed for 15 minutes. The supernatant is slowly poured into EtOH. A precipitate is formed immediately. Approximately 5-8 ml EtOH is needed to get 1 g powder. The EtOH solvent with powder is filtered, and an off-white powder is obtained. The powder is placed in a 50° C. oven for drying and an 88% yield of product is obtained. PXRD confirms the purity of ZLC powder compared to ZLC crystal.

Example 2

Dentifrice with ZLC

Dentifrice compositions comprising ZLC were prepared having the formulations as indicated in Table 1.

TABLE 1

| Ingredients (wt. %) | Formula A | Formula B | Formula C |
|---|---|---|---|
| Sodium fluoride | 0.32 | 0.32 | 0.32 |
| Zinc oxide | 1.05 | 1.05 | 1.05 |
| HCL 37% | 0.68 | 0.68 | 0.68 |
| Lysine HCl | 4.72 | 4.72 | 4.72 |
| 85% Phosphoric acid | 0.2 | 0.2 | 0 |
| Sodium Hydroxide 50% | 0 | 0 | 0.5 |
| Sodium Saccharin | 0.8 | 0.2 | 0.2 |
| Sucralose | 0 | 0.02 | 0.02 |
| Titanium dioxide | 0.4 | 0.4 | 1 |
| Sodium CMC-type 12 | 0.2 | 0.5 | 0 |
| Xanthan gum | 0.4 | 0 | 0 |
| Plasdone K90 (PVP) | 0 | 1 | 1 |
| Hydroxyethyl cellulose | 0 | 0 | 0.2 |
| Surfactants | 2.75 | 2.75 | 2.75 |
| Silica | 21 | 19 | 26 |
| Glycerin | 42.28 | 43.5 | 36.1 |
| Polyethylene glycol 600 | 3 | 3 | 3 |
| Propylene glycol | 4 | 4 | 4 |
| STPP | 2 | 2 | 2 |
| Flavor | 1.2 | 1.7 | 1.45 |
| Deionized water | 15 | 15 | 15 |
| pH of the formulation | 7.6 | 7.6 | 8.2 |

The dentifrice compositions contained different thickening agents. Formula A contained 0.2% sodium CMC and 0.4% xanthan gum. Formula B contained 0.5% sodium CMC and 1% polyvinylpyrrolidone (PVP). Formula C contained 0.2% hydroxyethyl cellulose and 1% PVP. Formula C was heated for about 1 hour at 80° C. during the making process in order to fully dissolve and hydrate hydroxyethyl cellulose. Formula A and B were not heated during the making process, because neither xanthan gum nor CMC requires heating. The dentifrice compositions were subjected to an aging study to determine any change in rheological properties over time. The dentifrice compositions were subjected to a temperature of 40° C. or 25° C. The yield stress was measured at initial, 4, 8, and 13 weeks. The yield stress quantifies the amount of stress that the fluid may experience before it yields and begins to flow and is therefore a measure of squeezability (resistance to flow upon applied pressure). The yield stress was measured using Brookfield Model RVT viscometer, Spindle V74. Measurements are presented in Table 2.

TABLE 2

| Formulation | Ysup (Pa) | | | |
|---|---|---|---|---|
| | initial | 4 weeks | 8 weeks | 13 weeks |
| Formula A at 40° C. | 470 | 1300 | unreadable | unreadable |
| Formula B at 40° C. | 470 | 300 | not measured | 1536 |
| Formula C (with heat) at 40° C. | 29.8 | 165 | 127 | 156 |
| Formula C (with heat) at 25° C. | 29.8 | 96.7 | 130 | 140 |

The yield stress of formula A containing 0.2% CMC and 0.4% xanthan gum became unacceptably high after 8 weeks at 40° C. Unlike formula A, formula B containing 0.5% sodium CMC and 1% PVP did not become unsqueezable over the period of the test. However, the yield stress of formula B still increased over time so that formula B became difficult to dispense from the dispenser after 13 weeks at 40° C., showing that although the incorporation of PVP into the composition improves the rheological property of the composition, it is insufficient to maintain acceptable yield stress over time. In contrast, formula C containing 0.2% hydroxyethyl cellulose and 1% PVP maintained acceptable yield stress over a period of 13 weeks at 40° C. and 25° C.

The viscosity of formula C was also measured. The dentifrice composition was subjected to a temperature of 40° C. and 25° C. and the yield stress was measured at initial, 4, 8, and 13 weeks. The viscosity was measured using a Brookfield Model RVT viscometer, Spindle V74. The results are shown in Table 3.

TABLE 3

| Formulation | cps (mPas) | | | |
|---|---|---|---|---|
| | initial | 4 weeks | 8 weeks | 13 weeks |
| Formula C (with heat) at 25° C. | 431553 | 456029 | 508202 | 421247 |
| Formula C (with heat) at 40° C. | 431553 | 464402 | 642820 | 600953 |
| Formula C (no heat) at 25° C. | 304019 | 253135 | 326277 | 306596 |
| Formula C (no heat) at 40° C. | 304019 | 306596 | 414162 | 425756 |

The composition was heated for about 1 hour at 80° C. or was not heated during the making process. The viscosity of formula C was increased when the composition was heated during the making process, suggesting that without heating during the making process, hydroxyethyl cellulose is not fully hydrated. Whether the composition was heated or not during the making process, the viscosity of formula C reached an acceptable steady state value and was maintained over the period of the test. In contrast, formula A and B continued to thicken progressively and became difficult to squeeze. These results suggest that chemical reactions occur between xanthan gum/CMC and other ingredients, e.g., ZLC, that are present in the composition, resulting in progressive thickening over time, whereas hydroxyethyl cellulose and PVP do not interact with other ingredients, e.g., ZLC, that are present in the composition.

It may be seen therefore that the thickening composition employed in accordance with the present invention enables the dentifrice composition comprising ZLC to exhibit acceptable rheological properties without progressive thickening over time.

While the disclosure has been described with respect to specific examples including presently preferred modes of carrying out the disclosure, those skilled in the art will appreciate that there are numerous variations and permutations of the above described systems and techniques. It is to be understood that other embodiments may be utilized and structural and functional modifications may be made without departing from the scope of the present disclosure. Thus, the scope of the disclosure should be construed broadly as set forth in the appended claims.

What is claimed is:

1. A dentifrice composition comprising
   a. a zinc-amino acid complex, wherein the zinc-amino acid complex is a zinc lysine chloride complex having the chemical structure $[Zn(C_6H_{14}N_2O_2)_2Cl]^+Cl^{31}$ ("ZLC"), either in solution of the cationic complex $([Zn(C_6H_{14}N_2O_2)_2Cl]^+)$ and the chloride anion, or in solid salt form, optionally in mono-or dihydrate form;
   b. a thickening system consisting of about 0.2% hydroxyethyl cellulose, about 1% polyvinylpyrrolidone, about 3% polyethylene glycol, and about 6% silica thickener, by weight of the composition;
   wherein the composition has a pH greater than 8.0.

2. The composition of claim 1, wherein the zinc-amino acid complex is present in an amount of 2-8% of the dentifrice by weight of the composition.

3. The composition of claim 1, wherein the pH of the composition is 8.0-8.5.

4. The composition of claim 3, wherein the pH of the composition is 8.1-8.3.

5. The composition of claim 1, wherein the composition comprises a fluoride ion source.

6. The composition of claim 1, wherein the composition comprises one or more soluble phosphate salts.

7. The composition of claim 6, wherein the one or more soluble phosphate salts comprise tetrasodium pyrophosphate (TSPP), sodium tripolyphosphate (STPP) or a combination of TSPP and STPP.

8. The composition of claim 1, wherein the composition comprises water in the amount of 10-20% by weight of the dentifrice.

9. The composition of claim 1, wherein the composition comprises ingredients selected from one or more of abrasives, buffering agents, humectants, surfactants, gum strips or fragments, breath fresheners, flavoring, fragrance, coloring, antibacterial agents, whitening agents, agents that interfere with or prevents bacterial attachment, calcium sources, and potassium salts.

10. The composition of claim 1, wherein the composition comprises sodium lauryl sulfate.

11. The composition of claim 1, wherein
   the zinc-amino acid complex is ZLC in an amount of 2-8% by weight of the composition; and
   the composition further comprises
   a fluoride ion source, silica abrasives,
humectant,
one or more soluble phosphate salts,
anionic surfactant,
zwitterionic surfactant,
flavoring, sweetener and 10-18 wt. % water; and
the pH of the composition is 8.1-8.3.

12. A method of treating or reducing dental enamel erosion, cleaning the teeth, reducing bacterially-generated biofilm and plaque, reducing gingivitis, inhibiting tooth decay and formation of cavities, and/or reducing dentinal hypersensitivity comprising applying a dentifrice according to claim 1 to the teeth.

* * * * *

UNITED STATES PATENT AND TRADEMARK OFFICE
CERTIFICATE OF CORRECTION

PATENT NO.       : 10,576,033 B2
APPLICATION NO.  : 15/756362
DATED            : March 3, 2020
INVENTOR(S)      : Gregory Szewczyk et al.

It is certified that error appears in the above-identified patent and that said Letters Patent is hereby corrected as shown below:

On the Title Page

In the item "(56) References Cited", under "FOREIGN PATENT DOCUMENTS", Line 2, "WO-9112517" should be replaced with –WO-9912517–.

In the Specification

Column 5, Line 10, "e g.," should be replaced with –e.g.,–.

Column 12, Line 26, "thereof in" should be replaced with –thereof. In–.

Column 15, Line 25, "&." should be replaced with –&–.

Column 15, Line 47, "Polyox®," should be replaced with –Polyox®–.

In the Claims

Column 20, Line 27, in Claim 1, "$[Zn(C_6H_{14}N_2O_2)_2Cl]^+Cl^{31}$" should be replaced, with –$[Zn(C_6H_{14}N_2O_2)_2Cl]^+Cl^-$–.

Signed and Sealed this
Second Day of June, 2020

Andrei Iancu
*Director of the United States Patent and Trademark Office*